US008036911B2

(12) United States Patent
Bellon et al.

(10) Patent No.: US 8,036,911 B2
(45) Date of Patent: Oct. 11, 2011

(54) SYSTEM AND METHOD FOR MANAGING PATIENT CARE THROUGH AUTOMATED MESSAGING

(75) Inventors: Lauren L. Bellon, San Diego, CA (US); Thuy T. Nguyen, Carlsbad, CA (US); Barry A. Brown, Encinitas, CA (US)

(73) Assignee: CareFusion 303, Inc., San Diego, CA (US)

( * ) Notice: Subject to any disclaimer, the term of this patent is extended or adjusted under 35 U.S.C. 154(b) by 1208 days.

(21) Appl. No.: 11/270,990

(22) Filed: Nov. 11, 2005

(65) Prior Publication Data

US 2007/0112602 A1 May 17, 2007

(51) Int. Cl.
*G06Q 50/00* (2006.01)

(52) U.S. Cl. .................................. 705/2; 705/3
(58) Field of Classification Search .................. 705/2, 3, 705/4
See application file for complete search history.

(56) References Cited

U.S. PATENT DOCUMENTS

| 5,291,399 | A | 3/1994 | Chaco |
| 5,465,082 | A | 11/1995 | Chaco |
| 5,703,786 | A | 12/1997 | Conkright |
| 5,754,111 | A | 5/1998 | Garcia |
| 5,822,544 | A | 10/1998 | Chaco et al. |
| 5,867,821 | A | 2/1999 | Ballantyne et al. |
| 5,902,234 | A | 5/1999 | Webb |
| 5,942,986 | A | 8/1999 | Shabot et al. |
| 6,004,020 | A * | 12/1999 | Bartur ........................... 700/236 |
| 6,092,102 | A | 7/2000 | Wagner |
| 6,277,071 | B1 * | 8/2001 | Hennessy et al. ............. 600/300 |

(Continued)

FOREIGN PATENT DOCUMENTS

JP 02004320555 11/2004

OTHER PUBLICATIONS

International Preliminary Report on Patentability PCT/US2006/043293 dated May 14, 2008.

(Continued)

*Primary Examiner* — Gerald J. O'Connor
*Assistant Examiner* — Edward Winston, III
(74) *Attorney, Agent, or Firm* — McDermott Will & Emery LLP

(57) ABSTRACT

A system and method in accordance with the invention allow a user to select when messages relating to medication events are sent and to select the content parameters of those messages. In one aspect, a user selects certain event types, the occurrence of which will cause a message to be sent to the user. For example, the user may select a message type that pertains to the availability of a medication in an automated dispensing machine for that user's patient. In another aspect, the user may customize the contents of the message to include or exclude certain information. For example, the user may desire the message to indicate only the patient's name and not the patient's gender or age. In yet another aspect, the user may filter messages so that only certain messages are sent. For example, the user may select a filter that permits only messages pertaining to his or her patients to be sent. The system further comprise a user interface disposed on an automated dispensing machine that enables a user to configure the messaging system as he or she desires. A method in accordance with the invention comprises selecting medication event types about which a message will be sent to the user, the content of the message, and filters for messages.

32 Claims, 10 Drawing Sheets

U.S. PATENT DOCUMENTS

| | | |
|---|---|---|
| 6,611,806 B1 | 8/2003 | Harvey |
| 6,859,134 B1 | 2/2005 | Heiman et al. |
| 7,917,374 B2 * | 3/2011 | Walker ................ 705/2 |
| 7,917,375 B2 * | 3/2011 | Ohmura et al. ........... 705/2 |
| 2001/0044731 A1 | 11/2001 | Coffman et al. |
| 2002/0032582 A1 * | 3/2002 | Feeney et al. ............ 705/2 |
| 2002/0147526 A1 | 10/2002 | Siegel |
| 2003/0067386 A1 | 4/2003 | Skinner |
| 2004/0015132 A1 * | 1/2004 | Brown ................ 604/131 |
| 2004/0019505 A1 * | 1/2004 | Bowman et al. .......... 705/2 |
| 2004/0039607 A1 | 2/2004 | Savitz et al. |
| 2005/0002499 A1 | 1/2005 | Ordielle et al. |
| 2005/0021369 A1 | 1/2005 | Cohen et al. |
| 2005/0065817 A1 | 3/2005 | Mihai et al. |
| 2005/0065822 A1 | 3/2005 | Ying et al. |
| 2005/0070312 A1 | 3/2005 | Seligmann et al. |
| 2005/0086072 A1 | 4/2005 | Fox, Jr. et al. |

OTHER PUBLICATIONS

PCT International Search Report for International Application No. PCT/US2006/043293 mailed Oct. 16, 2007.

* cited by examiner

Please type in a Pager Number and Pin and then select the Manufacture you wish to use Available Manufactures:

Add pager for Area: ABRA

Pager Number: _____ 132

| | Manufacturer | Model | Protocol |
|---|---|---|---|
| Add Manufacturer 134 | | | |
| Select | Motorola | M2222 | TAP |
| Select | Nokia | N2222 | ATT Wireless |
| Select | QualComm | Q2222 | Generic |
| Select | Sprint | S2222 | SkyWord |
| Select | ujkj | ikty | SkyPage |

Add  Cancel

| Page Setup | Messaging Device | Message Event | Instant Message | Reports |

Enter Message:
[                    ] — 148

Areas: [All Areas ▼] — 150

☐ Select All Online Users — 152

[Send]

| Select | Area | Activated For | Status |
|--------|------|---------------|--------|
| ☐ | ABRA | WILLIAMS, CAROLYN RPH | OFFLINE |
| ☐ | ABRA | KENNEDY, EILEEN | OFFLINE |
| ☐ | C 1N | BARKES, JANET | OFFLINE |
| ☐ | C 4ALL | EVANS, KATHLEEN | OFFLINE |
| ☐ | C 1N | BRAY, MELANIE | OFFLINE |
| ☐ | ABRA | AAA, BBB | OFFLINE |
| ☐ | C 4N | AGYECUM, VICKIE | OFFLINE |
| ☐ | ABRA | ---,,aaa, aa | OFFLINE |

| | | | | | |
|---|---|---|---|---|---|
| Page Setup | Messaging Device | Message Event | Instant Message | Reports | |
| 100 | 116 | 118 | 120 | 122 | |

Start [Mar ▾] / [15 ▾]
End [Apr ▾] / [15 ▾]
156

Events ☐ All Events — 166
☑ New Patient Admit/Transfer
☑ Discharge Patient
☑ New/Modify Order
☑ Discontinued Order
☑ Discrepancy Found
☑ Discrepancy Resolved
☑ Pharmacy Instant Message Sort By ⦿ User Name
          ○ Date Areas ☐ All Areas — 162
☑ ABRA
☑ C 1N
☑ C 4ALL
☑ C4N
☑ C 4N0
☑ C 4S
☑ C 5N

[View Report] — 170

Users ☐ All Users — 164 / 158

| User Name | User ID |
|---|---|
| ☐ ---,,aaa, aa | TESTA |
| ☐ ---ANDERSON, DEBORAH | ANDERSONDE |
| ☐ 14320, 14320 | WWW |
| ☐ AAA,BBB | WWYMCD |
| ☐ AAAA, AAAAAAAAAAAAAAA | AAAAAAAAA |
| ☐ AAAB, AA | A2 |
| ☐ ABBOTT, LEILA | ABBOTTL |

1 2 3 4 5 ...                                    1 2 3 4 5 ...

SYSTEM AND METHOD FOR MANAGING PATIENT CARE THROUGH AUTOMATED MESSAGING

FIELD OF THE INVENTION

The present invention relates generally to managing patient care, and more particularly, a system and method for managing patient care through automated messaging.

BACKGROUND OF THE INVENTION

Cellular or mobile telephones, personal digital assistants ("PDAs"), wireless text messaging devices, laptop computers, and other portable communication devices with text messaging capability have increasingly become a popular means of wireless, private and rapid communication of messages to users who are continually moving about. As used herein, the term "messaging device" refers generally to any portable communication device adapted to receive, transmit, store, and display a message. The message may take any form for communicating information, including text, code, graphics, and any combination of the foregoing. Typically, a message service provider receives a message intended for a particular messaging device associated with the message service provider. A network of transceiver stations and/or satellites, maintained by the message service provider, broadcasts the message. The messaging device receives the broadcasted message when in range of a transceiver station or satellite, and alerts the recipient with an audible, visual, or vibratory signal. In two-way messaging systems the messaging device is also adapted to send a message, which allows the first message recipient to reply to the sender of the initial message.

Rising material and operational costs and a shortage of nurses have put pressure on the healthcare facilities to implement systems to improve workflow. Systems comprising networked automated dispensing machines (herein referred to also as "ADMs") for dispensing drugs and related items have been known for a number of years, and by way of example, a form of a such system can be found in U.S. Pat. Nos. 5,014,875 and 6,021,392, the entire contents of which are incorporated herein by reference. ADMs typically include multiple drawers for containing a variety of items and are placed in various locations within a healthcare facility. All of the drawers are normally locked to prevent unauthorized access to the items therein. A control unit on the ADM may incorporate a computer having a processor, a keyboard, a display, and a memory to permit user entry of an authorized access code in combination with a patient name and an item designation. Upon entry of appropriate information, the drawer containing the designated item is unlocked to permit the item to be removed by the user. The unlocked drawer is then closed by the user, whereupon the control unit locks the drawer again and generates a detailed access record specifying, for example, the date and time, patient name, item designation, and name of the user who removed the item. The generated access record can be stored in memory, transmitted to a hospital central computer, and/or printed as a paper copy.

More sophisticated ADMs have a network connection to remote workstations, such as a pharmacy workstation also having a display screen, processor, and a keyboard, and to a central computer or server associated with one or more data bases that store item inventory information, medical orders issued by doctors, prescriptions, and other information related to patient care. Based on those orders and prescriptions received from doctors, the pharmacy staff arrange for required items, such as prescribed medications, to be prepared and loaded into appropriate ADMs within the healthcare facility. The items are placed into drawers in the ADMs for later removal and use by users of the ADM, such as nurses. A complicating factor is the dynamic nature of the patient care environment. New orders and prescriptions from doctors are continually being created and existing orders and prescriptions may be cancelled, or changed, which sometimes requires more immediate attention on the part of a nurse. Further, new patients are being admitted to the healthcare facility while others are being discharged. Additionally, a patient's medication, for which a nurse is responsible, may or may not yet have been loaded into an ADM and the nurse must continually check for its arrival so that it may be administered.

To keep abreast of new orders and prescriptions or changes in either in prior art systems, the nurse must proactively log into an ADM which can be located some distance away from a patient, and check, for example, to see if new prescriptions are available or if medications have arrived at the ADM to fill a prescribed medication order or to see if orders have been canceled or changed. In some instances, a nurse knows that a new order has been issued by a doctor but must wait for it to be processed by the pharmacy staff, wait for it to become active on the central computer, and wait for the medication or medications to be loaded into the ADM before the nurse can act upon it. To ascertain when this has occurred, the nurse must proactively check the ADM. In other instances, a nurse knows that a patient has been admitted or transferred to the nurse's assigned work area but must again wait for orders and prescriptions for that patient to be processed, to become active, and the patient's medication or medications to be loaded into the local ADM. These situations have required the nurse to repeatedly check the ADM to learn if the medications are now available at the ADM or to learn what other actions may need to be performed.

It would be desirable to provide such needed information to the nursing staff in a more efficient manner so that the nurses' workflow could be handled more smoothly. Instead of requiring a nurse to physically go to an ADM to repeatedly check it for information relevant to the nurse's work, it would be desirable to send the information to the nurse, wherever he or she may be. The nurse could then receive the information without having to physically go to a central point. The ability of the nurse to receive relevant information at other locations, preferably any location within his or her primary care-giving area, would be more desirable for smoother workflow. Additionally, it would be even more desirable if a nurse could receive only certain information pertinent to his or her activities, and if the content parameters of the messages to the nurse could be controlled by the nurse. That is, a customized information notification system and method could increase the efficiency of the nursing staff and make their workflow go more smoothly.

Hence, those skilled in the art have recognized a need for a system and a method that improves the workflow of healthcare personnel by automatically providing them with timely information on events requiring their attention at their locations instead of at a single location. Furthermore, those skilled in the art have recognized a need for customized messages and message information for the nursing staff and other healthcare personnel. The present invention satisfies these and other needs.

SUMMARY OF THE INVENTION

The present invention provides for a system and method for improving workflows by more efficiently managing patient care. Automated messaging regarding medication dispensing events is provided.

Briefly and in general terms, there is provided a system for notifying users of the occurrence of medication supply events, the system comprising a medication dispenser that generates a medication supply event signal representative of the occurrence at the dispenser of a medication supply event, a memory in which may be stored user-selected event types, a messaging processor adapted to receive medication supply event signals from the medication dispenser, compare the received medication supply event signals to any user-selected event types in the memory, if the comparison indicates that the medication supply event signals received by the messaging processor correspond to a user-selected event type in the memory, send a message to a user that the event has occurred, and a messaging device carried by the user that is adapted to receive the message from the messaging processor and to communicate the received message to the user.

In more detailed aspects, the memory may also store user-selected message parameters, and the messaging processor is adapted to access the memory for any user-selected message parameters if the comparison indicates that the medication supply event signals received by the messaging processor correspond to a user-selected event type in the memory, and send a message to a user that the event has occurred, the message being provided in accordance with user-selected message parameters located in the memory. In yet a further aspect, the user-selected event type comprises a dispenser-specific event. And in further detailed aspects, the dispenser-specific event comprises an identification of an item available in the medication dispenser, and/or the dispenser-specific event comprises an identification of an item removed from the medication dispenser. In another aspect, the user-selected event type comprises a patient-specific event, and wherein the patient-specific event comprises an identification of a patient's name. In further aspects, the user-selected event type comprises a healthcare facility-specific event and the healthcare facility-specific event comprises an identification of a room in which a patient is located.

Turning now to other aspects, the memory may also store user-selected filters, the messaging processor is adapted to compare the received medication supply event signals to any user-selected filters in the memory, and if the comparison indicates that the medication supply event signals received by the messaging processor satisfy any stored user-selected filter in the memory, send a message to a user that the event has occurred. In a more detailed aspect, a user-selected filter comprises sending only events to the user that are related to that user's patient.

In another aspect in accordance with the invention, the messaging processor is integral with the dispenser. In a different aspect, the messaging processor is located remotely from the medication dispenser and further comprising a second processor located at the medication dispenser adapted to detect medication supply event and provide medication supply event signals from the medication dispenser to the messaging processor.

In yet another system aspect, the messaging processor is further adapted to require a response to the message and if a response is not received within a predetermined time, to send another message to a user that the event has occurred.

Also provided is a method of notifying users of the occurrence of medication supply events, the method comprising generating a medication supply event signal representative of the occurrence at a medication dispenser of a medication supply event, storing user-selected event types in a memory, receiving medication supply event signals from the medication dispenser, comparing the received medication supply event signals to stored user-selected event types, if the comparison indicates that the medication supply event signals received by the messaging processor correspond to a user-selected event type in the memory, sending a message to a user that the event has occurred, and receiving the message from the messaging processor by means of a messaging device carried by the user and communicating the received message to the user.

Other features, aspects, and advantages of the present invention will become apparent from the following detailed description, taken in conjunction with the accompanying drawings, which illustrate, by way of example, the principles of the invention.

BRIEF DESCRIPTION OF THE DRAWINGS

FIG. 7 provides sub-control user-selectable parameters derived from those parameters of FIG. 6 in which "Add Messaging device" was selected and provides a means for entering a pager number for a messaging device and for specifying a messaging device type;

FIG. 9 shows yet another control screen for entering controls into the computer program in accordance with aspects of the invention, in which text messages may be sent to selected users; and FIG. 10 is the last in the representative and exemplary series of control pages for providing user-selections over the embodiment of a computer program in accordance with aspects of the invention in which reports may be generated by entering controls through a View Report screen showing a means for generating a report of messages sent based on the names of message recipients, event types, and work areas.

DETAILED DESCRIPTION OF PREFERRED EMBODIMENTS

Figure 1:
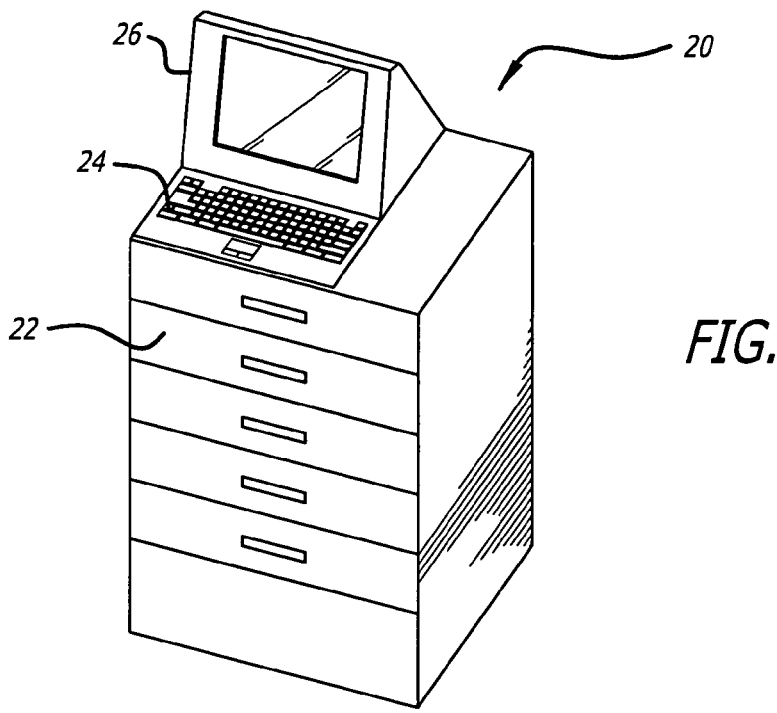
FIG. 1 is a perspective view of an automated dispensing machine ("ADM") having locking drawers within which medications for particular patients, or general medications may be stored and removed, the ADM also having a processor, keyboard, and display at which patient-related data may be accessed and viewed, and user-selected data may be input to the system, the processor being connected to a healthcare facility in this embodiment.

Referring now in more detail to the drawings in which like reference numerals indicate like or corresponding elements among the several views, there is shown in FIG. 1 an exemplary computerized automatic dispensing machine ("ADM") 20 having drawers 22 in which patient-specific medications and in some cases, general medications, are stored. The drawers are locked and may only be opened by the correct entry into the ADM of the name of an authorized user and password, and in some cases additional information. For the control over such activities, the ADM includes a computer having a keyboard 24, a display screen 26, a processor (not shown), and a memory (not shown). The ADM in this embodiment is also connected to a network within the healthcare facility which permits information to be communicated between the ADM and other devices on the network. The display screen and keyboard also provide users of the ADM an interface to a control program that controls the ability to send messages to users upon the occurrence of medication, patient, and other events and to control the content of those messages, as is described in detail below. As such, the ADM functions as a control point for both information and materials within a healthcare institution.

Figure 2:
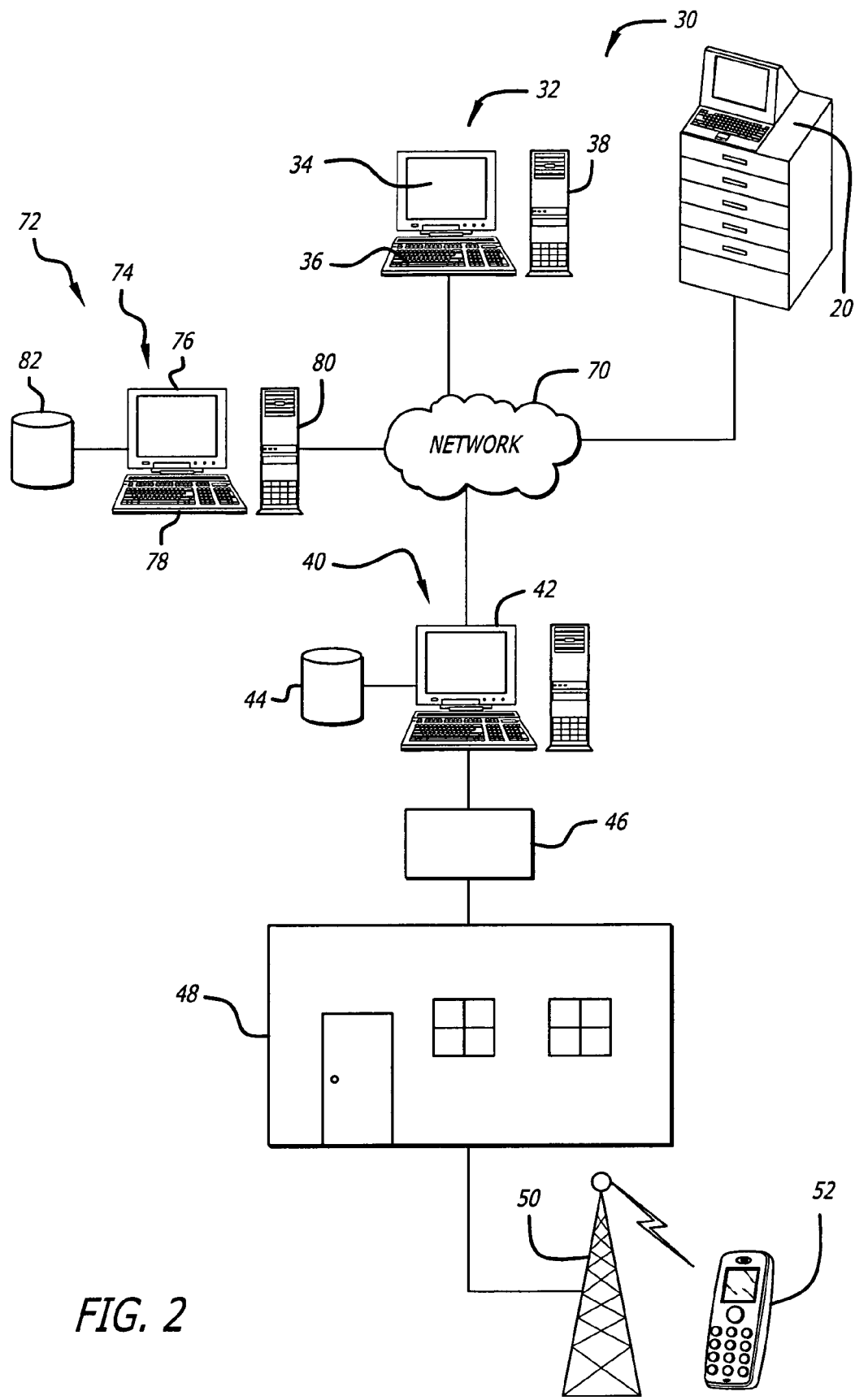
FIG. 2 is a diagram of an embodiment of a system for managing patient care in accordance with aspects of the invention and shows the ADM of FIG. 1 connected through its processor to a network, to which is also connected another processor remotely located from the ADM, a server, and a messaging processor connected to an external messaging device system.

Referring now to FIG. 2, there is shown a system for managing patient care 30 in accordance with an embodiment of the invention. The care management system comprises one or more ADMs 20, with only one being illustrated for convenience and clarity of illustration. Several ADMs may, for example, be conveniently distributed throughout the various patient care areas of a healthcare institution. The care management system further comprises one or more remote workstations 32 such as a pharmacy or administrative workstation, and at least one messaging server 40. In one case, the messaging server comprises a ProCAR workstation.

The remote workstations 32 each comprise a display screen 34, a data entry means, such as a keyboard 36, and a processor 38 with a memory (not shown). The messaging server 40 includes a messaging computer generally indicated as numeral 42 (which may include a display, keyboard, processor, memory, and other devices), an associated messaging data base 44, and a wired or wireless data communication means 46, such as a MODEM for example, for communicating with a message service provider 48. The message service provider communicates wirelessly through an antenna 50 for example, with one or more messaging devices 52 that are configured to receive, store, and display a message. The messaging device may also be configured to transmit a message. Only one messaging device is illustrated in this figure also for convenience and clarity of illustration although many may be serviced by one message service provider.

Figure 2A:
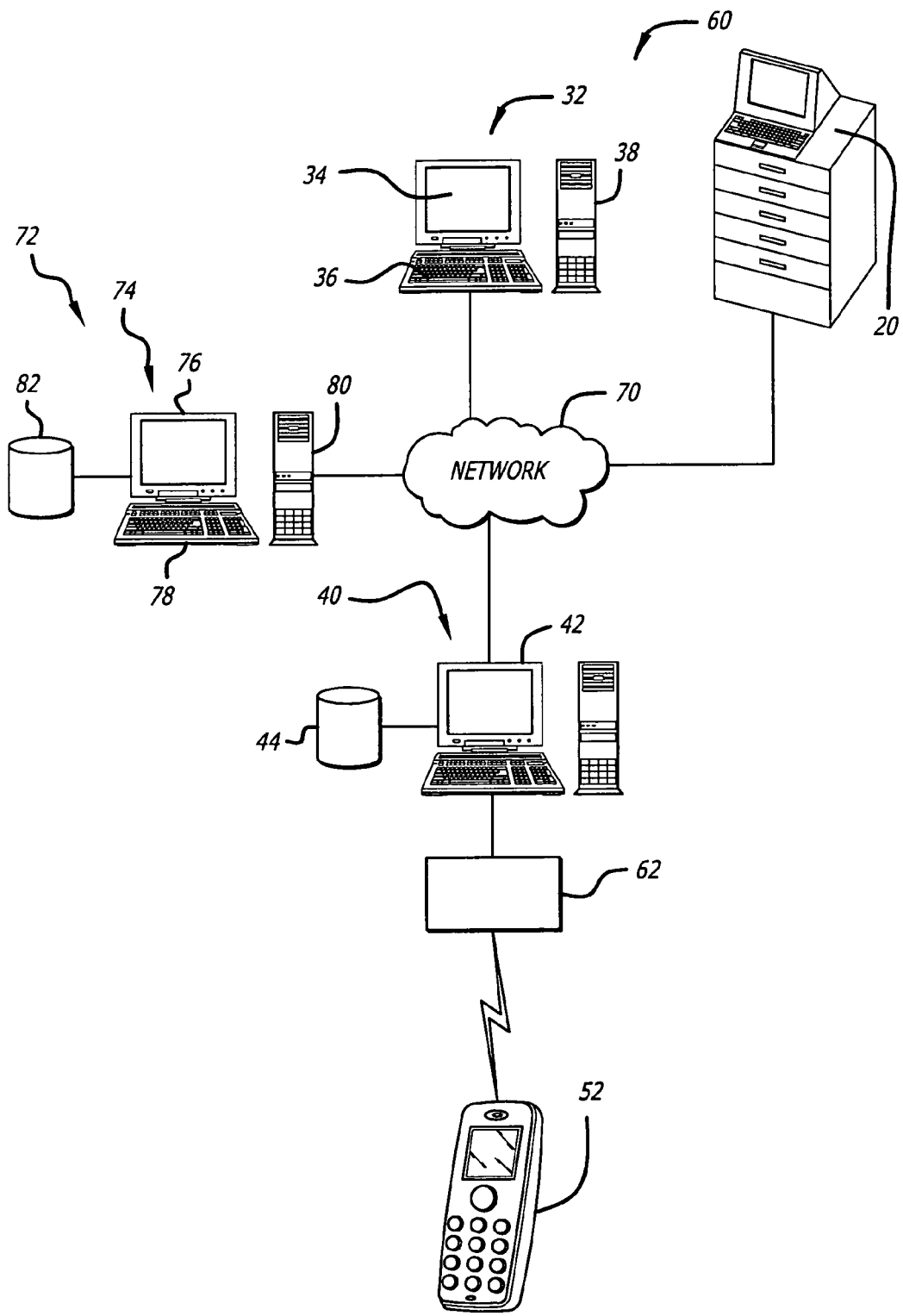
FIG. 2A is a diagram of an alternative embodiment of a system for managing patient care similar to that shown in FIG. 2 but for the lack of a connection to an external messaging system, and instead using its own messaging transceiver connected with the network.

It will be appreciated that wireless communication between the messaging server 40 and the messaging device 52 may be accomplished without a commercial message service provider 48 transmitting over long range antennas 50 as shown in FIG. 2. Other wireless communication methods may be used such as, for example, those utilizing IEEE 802.11 (e.g., Wireless Fidelity), IEEE 802.15 (e.g., Bluetooth) standards and others. As shown in FIG. 2A, for example, a commercial message service provider is not used. Instead, a system 60 has a messaging workstation 40 that has a transceiver 62. A communication zone is set up around the transceiver within which messaging devices 52 are able to receive messages and send replies. Several transceivers can be arranged throughout the facility to establish a larger communication zone.

The ADM 20, the remote workstation 32, and the messaging workstation 40 communicate together over a network 70 and with other devices, such as a hospital information system ("HIS") server 72. The network may take many forms such as the Internet or a local or wide area network, or other. Such network communication may be made through conventional wire connections, fiber optic connections, or through wireless methods, such as for example, those utilizing IEEE 802.11 and IEEE 802.15 standards. The HIS server 72 receives and stores data relating to patient medical records, doctors' orders, and contents of the ADM. The HIS server 72 shown in FIGS. 2 and 2A comprises a computer 74 having a 76, a keyboard 78, a processor 80, and a server data base 82 for storing the data.

The system 30 and 60 is adapted to run computer program code that provides a user-interface for inputting message criteria and executes a messaging operation comprising generating, storing, and sending messages. The ADM 20, the remote workstation 32, the messaging workstation 40, and/or the HIS server 72 may have associated memory such as RAM and/or ROM, and other computer-readable storage devices for storing segments of the computer program code, message criteria, and other parameters discussed below.

Figure 3:
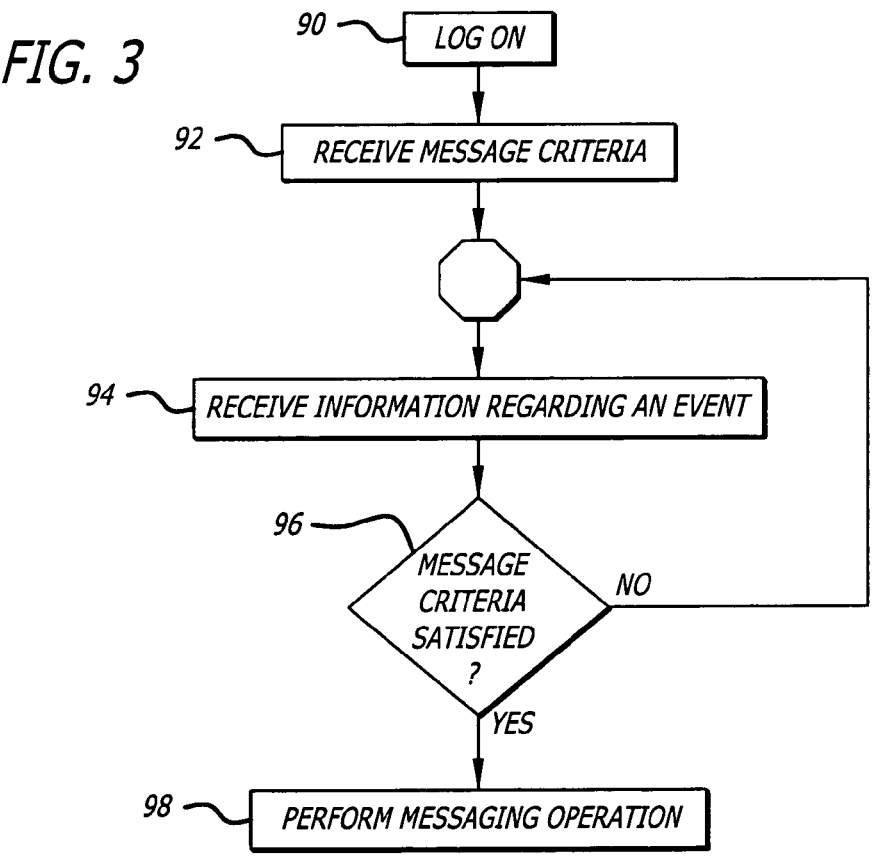
FIG. 3 is a workflow diagram illustrating in general a method for managing patient care in accordance with aspects of the invention.

Referring now to FIG. 3, there is shown an embodiment of a method of managing patient care in accordance with aspects of the invention. For convenience of discussion, the method of FIG. 3 will be described in connection with the system 30 of FIG. 2 although it will be appreciated that other systems may be used to implement the method. Initially at block 90 of the diagram, a user logs into the HIS server 72 from the ADM 20 in this embodiment by entering a recognized user name and access code and, in some cases, further information. Thereafter, the system 30 receives message criteria from the user at block 92 when the user configures the system as described in more detail below in connection with FIGS. 4 through 10. The message criteria and other setup variables selected by the user may be stored in one or more computer-readable storage devices, such as a memory, associated with the ADM, the messaging workstation 40, and/or the HIS server 72, or other device or devices.

Among other values, the message criteria may include a field for entry of an event type selected by the user. A message will be sent to the user upon the occurrence of an event that corresponds to one of the event types selected by the user. Such event types can include, for example, values, characters, or text representative of admittance or transfer of a patient, discharge of a patient, issuance of a new medical order for a patient, modification of a medical order for a patient, discontinuation of a medical order for a patient, identification of a medication that is newly available in an ADM, identification of a discrepancy in the tracking of items in an ADM, resolution of a discrepancy previously identified, and identification of a log-in failure at an ADM. Event types can also include, for example, reminders that notify a user that a medication was not removed from an ADM within a designated time period; reminders to check pain level, blood pressure, body temperature, or another physical parameter or parameters of a patient; notification to provide support for IV pumps and other medical equipment; and notification of a message initiated and composed by other individuals.

Such event types may be classified into categories. For example, medication supply and dispenser-specific events may relate to the status of the ADM and its contents. The user may desire to receive a message when an item is now available in the ADM. A user may desire to receive a message when a item has been removed from the ADM. Another category may comprise patient-specific events. For example, the user may desire to receive messages when a patient has been assigned to his or her care area. A user may desire to receive messages when a patient has been found to have high blood pressure. A further example of an event type is healthcare-specific events. For example, a user may desire to receive a message when a patient has been moved to a new room.

The message criteria can further include one or more filters, conditions, or rules that are specified by the user and are applied during processing to assist in determining the timing and control of a transmitted message. Such filters can include, for example, that a message regarding the new availability of a medication in an ADM be sent only if it is a medication for a user's patient, that a message regarding patient discharge be sent only when that event involves a patient that is under the care of the user, that a message regarding an ADM discrepancy be sent only when the discrepancy involves a narcotic medication, that a message regarding a new medical order be sent only when the order must be carried out immediately, and that a message regarding any event type be sent only when the user is on duty.

After a defined event occurs, information that describes that event is received by the system 30 at block 94 (FIG. 3) typically from manual entry or from an automated process. Manual entry may, for example, occur when a physician writes a patient's drug prescription on a slip of paper that is routed to a pharmacist who manually enters the prescription (e.g. the medication name, the dosage and the patient's name), with the keyboard 36 of a remote workstation 32. An automated process may, for example, involve a medication dispenser, such as an ADM or other type of medication dispensing device, connected to the network 70 and configured to automatically communicate when a medication has just been loaded into the ADM and is now ready for dispensing. In any case, the information received may be stored in the HIS server 72 data base 82 and typically includes an event type and time. Depending on the event type, the information may further include, for example, a patient name or identifier, a description of a medication, and/or an indication as to whether action must be taken immediately. For example, hospital staff may periodically reconcile items stored within an ADM 20 with inventory data in the server data base. Information on any such discrepancies would be entered into the system via the ADM 20, a remote workstation 32, or other device connected to the network 70. As a further example, a patient may be discharged and related information, such as patient name and room/bed designation, would similarly be entered and stored.

With continued reference to FIG. 3, at block 96 the HIS server 72 continuously monitors the server data base 82 for events that satisfy the user-selected message criteria. At block 98, the system 30 performs a messaging operation when an event satisfies the message criteria of one or more users. The messaging operation results in a message being sent to and received by the messaging devices 52 assigned to those users. Preferably, the message includes an event code and a message text. The event code may be whatever code a user specified as an indicator for a particular event type. For example, user "X" may specify "888" and user Y may specify "111" as their respective event codes for a patient discharge event. The message content may also include parameter types pre-selected by a user. For example, upon the occurrence of a patient discharge event, user "X" may have pre-selected patient name and room/bed location as parameters types to be included in a message, whereas user "Y" may have pre-selected patient name, room/bed location, date of birth, gender, and physician name. Accordingly, when a male patient named Bill Diamond occupying bed "B" of room 100 is discharged, the message for user "X" may appear as "888; Diamond, Bill; 100/B" and the message for user "Y" may appear as "111; Diamond, Bill; 100/B; Jul. 7, 1964; M; Dr. Nicole Green". Thus, the information contained in a message regarding a single event may vary from user to user.

In one embodiment of the present invention, the messaging operation 98 entails the server computer 72 providing message information to the messaging workstation 40 for each user whose messaging criteria is satisfied. The message information includes, for example, a time, a messaging device identification number or PIN (personal identification number) associated with the user, a communication protocol type of the messaging device assigned to the user, an event code, and message text. The system 30 may support communication protocol types suitable for one-way or two-way wireless communication such as, for example, Telelocator Alphanumeric Protocol (TAP), Simple Network Paging Protocol (SNPP), Wireless Communications Transfer Protocol (WCTP), Simple Mail Transfer Protocol (SMTP), and a host of proprietary protocols. For each set of message information received, the messaging workstation sends a corresponding message request to the message service provider 48. It is to be understood that more than one message service provider may be used simultaneously so as to accommodate a wide variety of messaging devices. The message request is encoded pursuant to the communication protocol specified in the message information. The message request can be sent via a public switched telephone network, cellular wireless network, the Internet, or other means as appropriate for the particular message service provider 48 and the communication protocol. Upon receiving a message request, the message service provider transmits a message to the appropriate messaging device 52.

In a further embodiment of the present invention, the system 30 can be configured for two-way communication. In this aspect, message recipients can be prompted to send a reply message to the messaging workstation 40 in order to acknowledge receipt of the message. When no reply is received by the system, the system may send the message to the same user again or send a backup message to a backup user, such as a supervisor or a co-worker in the same work area. It is contemplated that the backup message can include an identification of the first message recipient along with an event code and event parameters. In yet another embodiment, the system may monitor the time that passes between the transmission of the message and the reception of a reply to the message. If a predetermined period of time has elapsed since the message was sent, the system may, as described above, resend the message to the same user or to a back user. In another embodiment, the message server 40 waits to receive an indication that an ADM event has occurred, such as, for example, removal of a medication, the occurrence of which is an indication that the message has been received. If the event does not occur, or does not occur within a predetermined period of time, the message server 40 may resend the message to the user or to a backup user. In an alternative embodiment, a verbal page may be sent over the loudspeakers of the healthcare facility when users fail to send a required reply or acknowledgment within a predetermined period of time.

Figure 4:
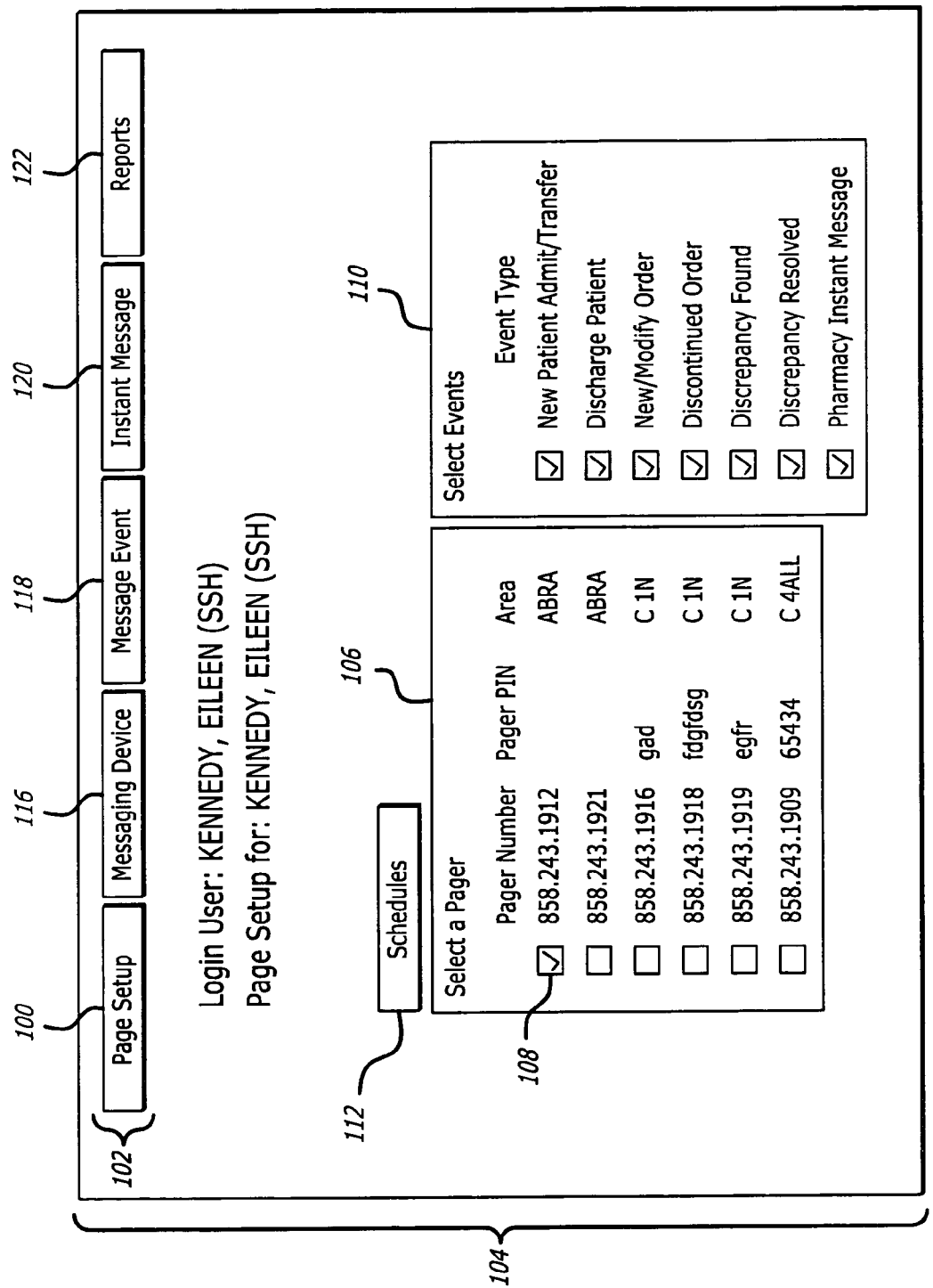
FIG. 4 provides the first in a series of graphically-oriented medication-event and patient-event message generation input data pages produced by a processor running a computer program in accordance with aspects of the invention in which a user is able to provide user-selected event types and user-selected message parameters to the computer program regarding when event messages are created and sent and what information is included in those messages, and in this case, provides a "Page Setup" routine for specifying message event types.

As mentioned above, a user configures the system 30 by specifying message criteria and other variables, which are accessible from computer-readable storage devices in order to control the operation of the system. Configuration can be accomplished through web-based computer programs executed from the ADM 20, the remote workstation 32, or other terminal linked to the server. Such programs render various graphical pages on the display screen of the ADM, remote workstation, or terminal. From the graphical pages, the user can rapidly make selections from lists and manually enter information into fields. For example, as shown in FIG. 4, after logging onto the system, the user may use a pointing device, such as a mouse, to click a "Page Setup" button 100 on a menu rendered on the display screen 26, 34 (FIG. 2). Upon clicking the Page Setup button 100, a Page Setup screen 104 is rendered below the menu 102. The Page Setup screen allows the user to choose and assign a particular messaging device 52 to herself/himself among a list of inactive (i.e., unassigned) messaging devices 52 displayed in a left-side panel 106 of the Page Setup screen 104. Once assigned, the system 30 labels the messaging device as "active."

The Page Setup screen 104 and other screens described below allow the user to select parameters from a list or enter new values and parameters which are used by the system to program the processor to operate in accordance with the selected or entered parameters and new values.

The inactive messaging devices 52 in the left-side panel 106 of Page Setup screen 104 are identified, for example, with a unique 10-digit "pager number" such as may be used to establish a telephone call through a public switched telephone network, and a personal identification number ("Pager PIN"). Preferably, each messaging device 52 is associated with a particular department, group or work area. The user selects a messaging device that is associated with the department, group or work area in which the user will be working by placing a check mark 108 next to the pager number of that messaging device. After selecting the messaging device, the user then selects one or more event types from a list of event types displayed in a right side panel 110 of the Page Setup screen 104. By selecting event types from this list, the user configures the system to send a message to him or her upon the occurrence of an event that is included in the selected event types. It will be understood that only messages characterized as being of a selected type will be sent to the user.

Figure 5:
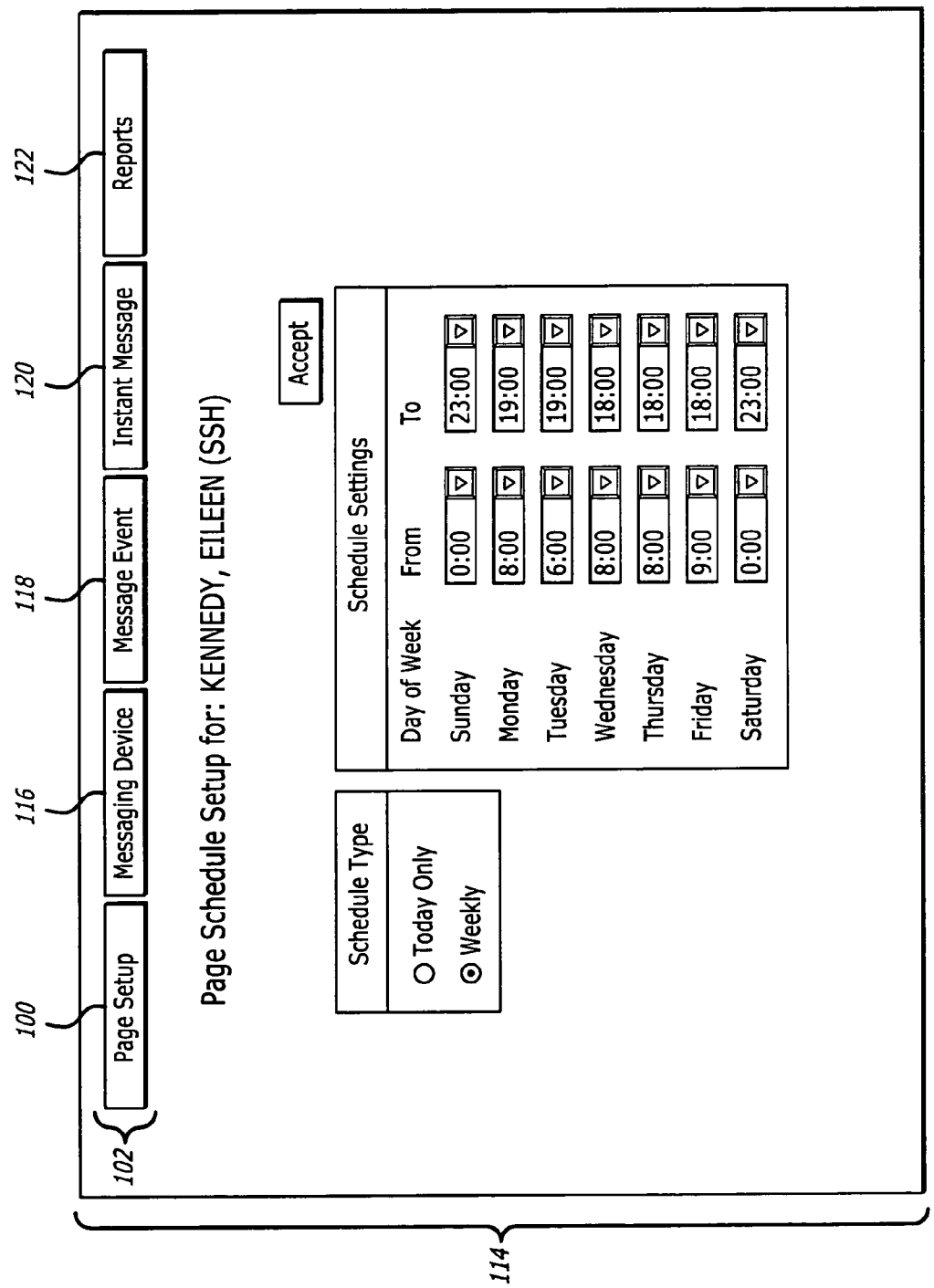
FIG. 5 provides the second in a series of user-selectable parameters for message generation in which the user may specify time periods within which messages are permitted to be sent.

After selecting one or more event types by placing a check mark in the appropriate box or boxes in the right side panel 110, the user may select a "Schedules" button 112 on the Page Setup screen 104 which causes a Page Schedule screen 114 to be rendered on the display 26, 34, as shown in FIG. 5. The Page Schedule screen 114 allows the user to specify time periods for each day of the week, within which messages are permitted to be sent to the user's messaging device 52. Accordingly, a message will be sent to the selected messaging device only if one of the selected event types occurs within the user-specified time periods.

Figure 6:
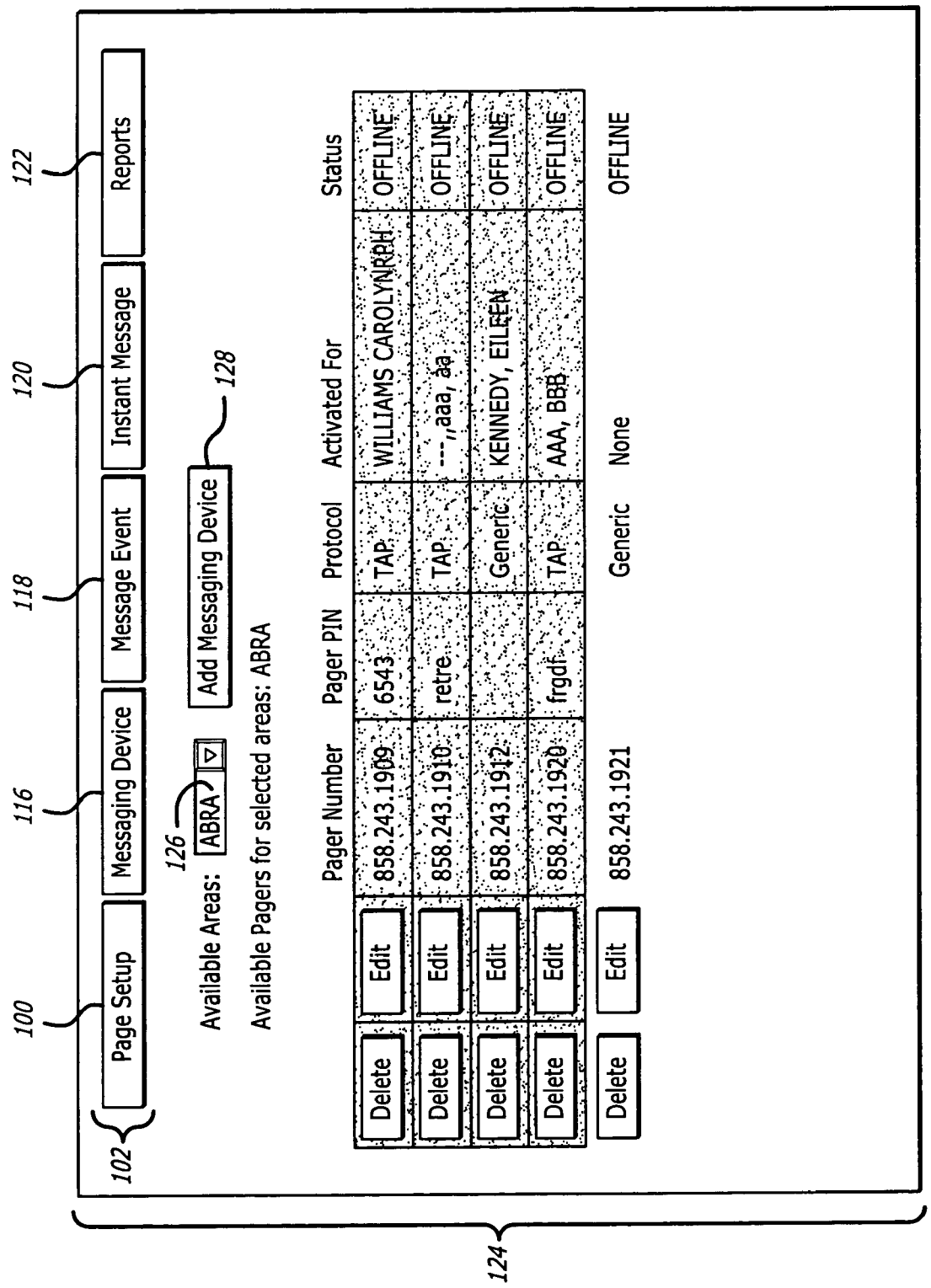
FIG. 6 is another in the series of user-selectable parameter pages for message generation showing controls over the "Messaging device" for adding, deleting, or editing settings for messaging devices.

A user may also add or delete messaging devices from the system 30. After logging into the system 30, the user may select the "Messaging device" button 116 on the menu 102. As shown in FIG. 6, a Messaging Device Setup screen 124 is then rendered which allows the user to add messaging devices, delete messaging devices, or edit the settings for assigned messaging devices for various work areas. A list of messaging devices available for deleting or editing is displayed after the user scrolls through and selects a work area from an Available Areas pull-down menu 126. The system 30 labels an assigned or active messaging device as being "online" during the user-specified time periods; all other messaging devices are labeled as being "offline". By selecting a work area using pull down menu 126, the user is presented with a display showing all of the available messaging devices that are associated with a particular work area. Thus, the user may select an available messaging device from a particular work area, or, alternatively, may choose to see a list of all available messaging devices in the entire institution.

To add a messaging device and begin the configuration process, the user clicks an Add Messaging Device button 128. When the Add Messaging Device button 128 is actuated, an Add New Messaging Device screen 130 is rendered on the display, as shown in FIG. 7. The Add New Messaging Device screen 130 provides text filed 88 into which the user enters a 10-digit number associated with the messaging device and to select a messaging device type according to manufacturer name, model number and communication protocol from a list of messaging device types supported by the system 30. The user may also add, edit or delete the types of messaging devices supported by the system 30 by selecting an "Add Manufacturer" button 134. These functions of adding and configuring a messaging device may be integrated into the front-end application or, alternatively, the back end as part of the paging engine.

Figure 8:
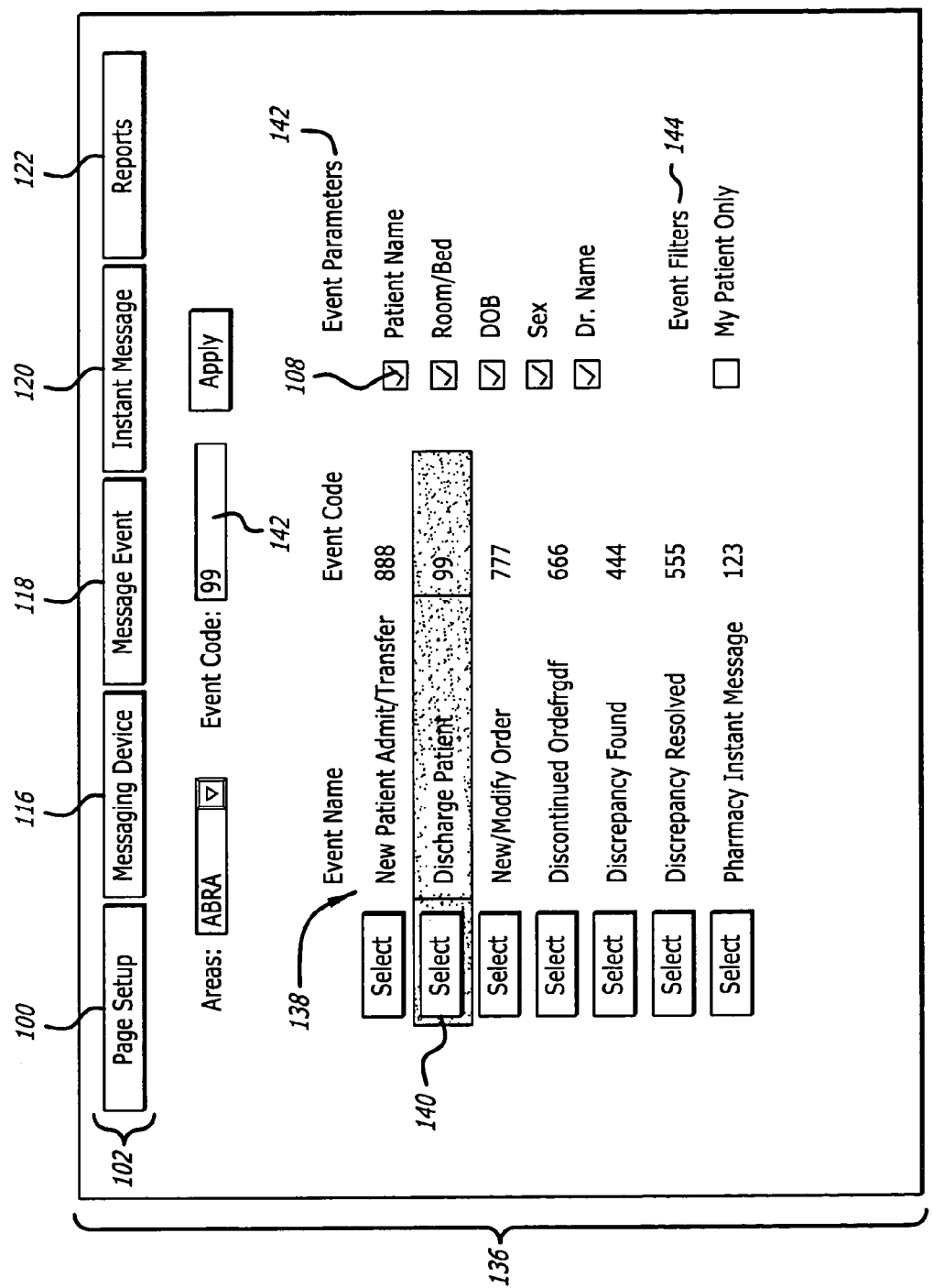
FIG. 8 is another embodiment of patient-event message control of a system and method in accordance with aspects of the invention in which "Page Event" was selected at the main menu bar (top of page) and provides a means for selecting event parameter types and event filters, the occurrence of which will cause a message to be sent by the system to the user under the user-selected conditions.

Referring now to FIG. 8, in order to specify types of event data or parameters that are to be included in a message, a user clicks on a "Message Event" button 118 on the menu 102 and a Message Event Setup screen 136 is rendered on the display 26, 34. The Page Event Setup screen 136 includes a list of event types ("Event Name") 138 previously specified for the user's messaging device, as described above in connection with FIG. 4. Each event type has a "Select" button 140 displayed next to it. Upon selecting an event type from the left side of the displayed screen, a list of available event parameter types ("Event Parameters") 142 is displayed on the right side of the screen.

The event parameter types available for selection on the right side of the Message Event Setup screen 136 depend on the event type selected from the list of event types displayed on the left side of the Message Event Setup screen 136. For example, if the Discharge Patient event type is selected, as illustrated by the shading in the figure, the list of available event parameters types associated with the selected event type (name) from the list 138 may, for example, be patient related, such as patient name, room/bed, DOB (date of birth), sex, and doctor's name. Alternatively, if the Discrepancy Found event type is selected, the list of event parameter types may, for example, be related to discrepancies in tracking items in the ADM 20 rather than being related to a particular patient.

In addition to selecting event parameter types, the user may enter a desired "Event Code" representing the event type into a text field 142. Preferably, a message received by the user will begin with an event code. By selecting, in this case, placing check marks 10, next to one or more event parameter types, the user selects the event parameter types that will follow the event code in a future message to the user. For example, a user can specify an event code of "99" for a Discharge Patient event type, and select only Patient Name and Room/Bed as event parameter types. Accordingly, the message "99; Diamond, Bill; 100/B" will be sent to this user when a patient named Bill Diamond occupying bed B of room 100 is discharged. It is to be understood that the message will be sent only during the time periods previously specified by the user as described in connection with FIG. 5.

A list of available event filters 144 is displayed when a user selects an event type from the Page Event Setup screen 136 shown in FIG. 8. The available event filters 144 can vary depending on the even type that is selected. For example, if the Discharge Patient event type is selected, the list of available event filters will be patient related. In particular, a patient related filter designated as "My Patient Only", as shown in FIG. 8, allows a user to restrict messages to events pertaining to patients under the care of that user. As a further example, if the New/Modify Order event type is selected, the list of available event filters can include "STAT Only" (immediate need) to allow the user to restrict messages to orders that are urgent and must be executed immediately. As another example, if the Discrepancy Found event type is selected, the list of available event filters can include the filter "Schedule II Only", allowing the user to restrict messages to discrepancies that involve a controlled substance such as morphine or codeine. Other event filters may be used as deemed appropriate by the healthcare institution.

In an alternative embodiment of the system as shown in FIG. 9, a user may initiate a message to be sent to a messaging device or group of messaging devices 52. The message can be sent from the ADM 20, the remote workstation 32, or other location programmed to allow the messaging function. After logging onto the system, such as for example, from the ADM or the remote workstation, the user selects an Instant Message button 120 on the menu 102, and an Instant Message screen 146 is rendered on the display screen. From the Instant Message screen 146, the user can enter a desired message into a an Enter Message text field 148." A list of persons with messaging devices that are online is displayed on this screen to allow the user to select recipients of the message entered in the Enter Message text field 148. The list of online users is configurable by the user from this screen. For example, the user can cause the system to list only persons who work within a particular work area by selecting that work area from an Areas pull-down menu 150. From the Areas list, the user selects individuals to receive the message. A "Select All Online Users" option box 152 allows the user to quickly specify that the message be sent to all persons with online messaging devices by placing a checkmark in the option box 152. It is contemplated that the Instant Message function can be used to notify users of an estimated time of arrival of a drug or time of some other event. The instant message function can also be used to notify users of rare or unusual events that are not included in the list of available event types described in connection with FIG. 4.

In another embodiment as shown in FIG. 10, the user may generate a report of messages sent by the system 30. The messages sent are stored in the messaging data base 44 (FIG. 2). After logging onto the system, the user selects a Report button 108 on menu 102 A Report screen 154 is then rendered as shown in FIG. 10. Using pull down menus 156, designated "Start" and "End," the user can scroll through and select a start date and an end date for the report. The Report screen also includes a User Name list 158 of potential message recipients (i.e., persons having messaging devices), a list of event types 160, and a list of work areas 162. From these lists, the user can customize the report to include messages sent to particular users by selecting one or more user names in list 158, messages for particular event types by selecting one or more event types from list 160, and/or messages to persons within a particular work area by selecting one of more areas from list 162. The user may enter check marks in check boxes 164, 166, 168 designated as "All Users," "All Events," and "All Areas" to quickly configure and customize the report to include all data. In addition, the user may further customize the report by sorting the messages in the report according to the names of recipients (designated "User Name") or by the dates the messages were sent (designated "Date"). Those skilled in the art will immediately understand that other indices for sorting may be used without departing from the scope of the present invention. The user may then generate the report for viewing and printing by pressing a View Report button 170.

As illustrated by the exemplary drawings, the present invention is embodied in a system for dispensing drugs and other healthcare items. The system provides for the automatic sending of messages upon the occurrence of events that satisfy certain message criteria. A message with information relevant to the event is generated automatically by the system or upon user initiation. The event may, for example, be of a type associated with an ADM, a type related to dispensing a healthcare item, or a type requiring patient care activity. Message criteria are specified by the user through an ADM or a remote workstation. A remote workstation may be, but is not limited to, a console workstation associated with the ADM or a personal computer located remotely from the ADM. The evaluation of events against message criteria is continuously performed by a computer program that is executed by a server in communication with the ADM and the remote workstation. The message is generated and transmitted by the server computer, to be ultimately received by messaging devices carried by or in proximity to one or more users.

From the foregoing, it will be appreciated that the system and method for managing patient care in accordance with the principles of the invention improves the workflow of users by automatically informing them of time critical events. Users are informed of only the types of events they have selected and are given only the types of information or event parameters they have selected. Thus, users avoid receiving any unnecessary messages that would only serve to distract them and to cause future messages to be ignored. With improved workflow, users have more time to provide direct care to patients, which improves patient safety. Also, the system and method of the invention results in more accurate and timely delivery of drugs and related items to patients and is particularly useful for users who are responsible for a high number of patients.

The system and method in accordance with the principles of the invention also provide for rapid and convenient message customization, which can be performed once or repeatedly to suit the needs of the user. The quantity and type of messaging devices operating within the system can also be easily changed along with the changing needs the healthcare institution. Such flexibility and ease of use also allows users to have more time to provide direct care to patients.

While several particular forms of the invention have been illustrated and described, it will also be apparent that various modifications can be made without departing from the scope of the invention. For example, any variety of suitable wireless communication methods between the server computer and the messaging device can be used to allow the messaging device to receive a message soon after the information about an occurred event is received. As a further example, any variety of suitable means for specifying message criteria may be used. It is also contemplated that various combinations or subcombinations of the specific features and aspects of the disclosed embodiments can be combined with or substituted for one another in order to form varying modes of the invention. For example, a message service provider may be used simultaneously with an IEEE 802.11 wireless local area network to send messages wirelessly to messaging devices. Accordingly, it is not intended that the invention be limited, except as by the appended claims.

We claim:

1. A system for notifying users of the occurrence of medication supply events, the system comprising:
a medication dispenser configured to securely store a plurality of medications and to allow access to the medications upon entry of an authorized access code, the medication dispenser further configured to generate a medication supply event signal indicative of the occurrence at the dispenser of one of a set of medication supply events relating to a medication prescribed to a patient, wherein the set of medication supply events includes at least one of:
issuance of a new medical order;
modification of a medical order; and
discontinuation of a medical order; wherein a medical order is an order issued by a caregiver;
a memory configured to store user-selected event types;
a messaging processor adapted to:
receive medication supply event signals from the medication dispenser;
compare the received medication supply event signals to any user-selected event types in the memory; and
send a message to a user of the medication dispenser via a communication link that the medical supply event has occurred based upon a determination that the comparison indicates that the medication supply event signals received by the messaging processor correspond to a user-selected event type in the memory; and
a messaging device carried by the user that is adapted to receive the message from the messaging processor and to communicate the received message to the user; wherein the system is configured such that authorized access codes are provided to caregivers who administer the medication to the patient but not to the patient receiving the medication.

2. The system of claim 1 wherein:
the memory is further configured to store user-selected message parameters; and the messaging processor is further adapted to:
access the memory for any user-selected message parameters; and send the message to a user that the event has occurred, the message being provided in accordance with user-selected message parameters located in the memory.

3. The system of claim 2 wherein a user-selected message parameter comprises an identification of a patient's name.

4. The system of claim 2 wherein user-selected message parameter types comprise: name of a patient, location of a patient, age of a patient, gender of a patient, name of a physician or description of a drug to be administered to the patient.

5. The system of claim 1 wherein a user-selected event type comprises an identification of an item available in the medication dispenser.

6. The system of claim 5 wherein the item comprises a medication that has just recently become available in the medication dispenser.

7. The system of claim 1 wherein the user-selected event types comprise discharge of a patient, issuance of a medical order for a patient, modification of a medical order for a patient, discontinuation of a medical order for a patient, identification of an item removed from the medication dispenser, identification of a discrepancy between items stored in a dispensing machine and items expected to be stored in the dispensing machine, resolution of a discrepancy at a dispensing machine, or identification of a log-in failure at a dispensing machine.

8. The system of claim 1, wherein:
the memory may also store a user-selected message filter;
the messaging processor is adapted to:
compare the received medication supply event signals to any user-selected message filters in the memory; and
send a message to a user that the event has occurred if the comparison indicates that the medication supply event signals received by the messaging processor satisfy any stored user-selected message filter in the memory.

9. The system of claim 8, wherein the user-selected message filter comprises sending only events to the user that are related to that user's patient.

10. The system of claim 1 wherein the messaging processor is integral with the dispenser.

11. The system of claim 1 wherein the messaging processor is located remotely from the medication dispenser and further comprising a second processor located at the medication dispenser adapted to detect medication supply events and provide medication supply event signals from the medication dispenser to the messaging processor.

12. The system of claim 1 wherein the messaging processor is further adapted to: require a response to a sent message; and send another message to a user that the event has occurred if a response is not received within a predetermined time.

13. The system of claim 12 wherein the response comprises an event generated by the medication dispenser.

14. The system of claim 1 wherein the set of medication supply events further includes an identification of a medication that is newly available in the medication dispenser.

15. A method of notifying users of the occurrence of medication supply events, the method comprising the steps of:
providing authorized access codes to caregivers who administer medications to a patient but not to the patient receiving the medication;
a medication dispenser generating a medication supply event signal indicative of the occurrence of one of a set of medication supply events at a medication dispenser configured to securely store a plurality of medications and to allow access to the medications upon entry of an authorized access code, the medication supply event relating to a medication prescribed to a patient, wherein the set of medication supply events includes at least one of:
issuance of a new medical order;
modification of a medical order; and
discontinuation of a medical order; wherein a medical order is an order issued by a caregiver;
storing user-selected event types in a memory;
receiving medication supply event signals from the medication dispenser;
comparing the received medication supply event signals to stored user-selected event types;
sending a message to a user of the medication dispenser via a communication link that the event has occurred based upon a determination that the comparison indicates that the medication supply event signals received by the messaging processor correspond to a user-selected event type in the memory;
receiving the message from the messaging processor by means of a messaging device carried by the user; and
communicating the received message to the user.

16. The method of claim 15, wherein:
the step of storing user-selected event types also comprises storing user-selected message parameters in the memory and accessing the memory for any user-selected message parameters;
and the step of sending a message to a user that the event has occurred comprises providing the message in accordance with user-selected message parameters.

17. The method of claim 16, wherein the step of storing a user-selected event type comprises storing an identification of a patient's name.

18. The method of claim 16, wherein the step of storing a user-selected event type comprises storing an identification of a room in which a patient is located.

19. The method of claim 16, wherein the step of providing the message in accordance with user-selected message parameters comprises providing an identification of an item available in the medication dispenser in the message.

20. The method of claim 19, wherein the step of providing the message in accordance with user-selected message parameters comprises providing an identification of a medication just recently made available in the medication dispenser in the message.

21. The method of claim 15, wherein the step of sending a message in accordance with a user-selected event type comprises providing an identification of an item removed from the medication dispenser.

22. The method of claim 15, wherein the step of storing user-selected event types in memory also comprises:
storing user-selected message filters;
comparing the received medication supply event signals to any stored user-selected message filters; and
sending a message to a user that the medical supply event has occurred if the comparison indicates that the received medication supply event signals satisfy any stored user-selected message filter in the memory.

23. The method of claim 22, wherein the step of sending a message when a user-selected message filter is satisfied comprises only sending a message about events to a user that are related to that user's patient.

24. The method of claim 15, wherein the step of comparing the received medication supply event signals to stored user-selected event types occurs at the medication dispenser.

25. The method of claim 15, wherein the step of comparing the received medication supply event signals to stored user-selected event types occurs remotely from the medication dispenser.

26. The method of claim 15, further comprising the steps of:
requiring a response to a sent message from a user; and
sending another message to a user that the event has occurred if a response is not received from a user within a predetermined time.

27. The system of claim 15 wherein the set of medication supply events further includes an identification of a medication that is newly available in the medication dispenser.

28. A system for notifying users of the occurrence of medication supply events, the system comprising:
an automated medication dispenser (ADM) coupled to a communication network, the ADM configured to securely store a plurality of medications and to allow access to the medications upon entry of an authorized access code, the ADM dispenser further configured to generate a medication supply event signal indicative of the occurrence at the dispenser of one of a set of medication supply events relating to a medication prescribed to a patient, wherein the set of medication supply events includes at least one of:
issuance of a new medical order;
modification of a medical order; and
discontinuation of a medical order, wherein a medical order is an order issued by a caregiver;
a memory configured to store user-selected event types, user-selected message parameters, and user-selected message filters;
a messaging processor adapted to:
receive the medication supply event signals from the medication dispenser;
compare the received medication supply event signals to user-selected event types in the memory; and
based upon a determination that the comparison indicates that the medication supply event signals received by the messaging processor correspond to a user-selected event type in the memory and that the event satisfies a message filter stored in memory, send a message to a user of the medication dispenser via a communication link that the event has occurred in accordance with user-selected message parameters contained in memory; and a messaging device carried by the user that is adapted to receive the message from the messaging processor and to communicate the received message to the user wherein the system is configured such that authorized access codes are provided to caregivers who administer the medication to the patient but not to the patient receiving the medication.

29. The system of claim 28 wherein a user-selected event type comprises an identification of an item available in the medication dispenser.

30. The system of claim 28 wherein the messaging processor is integral with the dispenser.

31. The system of claim 28 wherein the messaging processor is located remotely from the medication dispenser and the system further comprises a second processor located at the medication dispenser adapted to detect medication supply event and provide medication supply event signals from the medication dispenser to the network to the messaging processor.

32. The system of claim 28 wherein the set of medication supply events further includes an identification of a medication that is newly available in the medication dispenser.

* * * * *